United States Patent
Bao et al.

(10) Patent No.: US 11,154,279 B2
(45) Date of Patent: Oct. 26, 2021

(54) TRANSMIT GENERATOR FOR CONTROLLING A MULTILEVEL PULSER OF AN ULTRASOUND DEVICE, AND RELATED METHODS AND APPARATUS

(71) Applicant: BFLY Operations, Inc., Guilford, CT (US)

(72) Inventors: Liewei Bao, Westford, MA (US); Kailiang Chen, Branford, CT (US); Tyler S. Ralston, Clinton, CT (US); Nevada J. Sanchez, Guilford, CT (US)

(73) Assignee: BFLY Operations, Inc., Guilford, CT (US)

( * ) Notice: Subject to any disclaimer, the term of this patent is extended or adjusted under 35 U.S.C. 154(b) by 858 days.

(21) Appl. No.: 15/087,962

(22) Filed: Mar. 31, 2016

(65) Prior Publication Data
US 2017/0281138 A1  Oct. 5, 2017

(51) Int. Cl.
| | |
|---|---|
| *A61B 8/00* | (2006.01) |
| *G01S 7/52* | (2006.01) |
| *B06B 1/02* | (2006.01) |
| *G01S 15/89* | (2006.01) |
| *G10K 11/34* | (2006.01) |

(52) U.S. Cl.
CPC ............ *A61B 8/54* (2013.01); *A61B 8/42* (2013.01); *A61B 8/4427* (2013.01); *A61B 8/56* (2013.01); *B06B 1/0215* (2013.01); *G01S 7/5202* (2013.01); *G01S 15/8915* (2013.01); *G10K 11/341* (2013.01); *B06B 2201/51* (2013.01)

(58) Field of Classification Search
None
See application file for complete search history.

(56) References Cited

U.S. PATENT DOCUMENTS

| | | | |
|---|---|---|---|
| 5,622,177 A | 4/1997 | Breimesser et al. |
| 6,186,949 B1 | 2/2001 | Hatfield et al. |
| (Continued) | | | |

FOREIGN PATENT DOCUMENTS

| | | |
|---|---|---|
| CN | 101677804 A | 3/2010 |
| CN | 103153194 A | 6/2013 |
| (Continued) | | |

OTHER PUBLICATIONS

Agarwal et al., Single-Chip Solution for Ultrasound Imaging Systems: Initial Results. 2007 IEEE Ultrasonics Symposium. Oct. 1, 2007;1563-6.

(Continued)

*Primary Examiner* — Luther Behringer
*Assistant Examiner* — Farouk A Bruce
(74) *Attorney, Agent, or Firm* — Wolf, Greenfield & Sacks, P.C.

(57) ABSTRACT

Circuitry for ultrasound devices is described. A multi-level pulser is described, which can support time-domain and spatial apodization. The multi-level pulser may be controlled through a software-defined waveform generator. In response to the execution of a computer code, the waveform generator may access master segments from a memory, and generate a stream of packets directed to pulsing circuits. The stream of packets may be serialized. A plurality of decoding circuits may modulate the streams of packets to obtain spatial apodization.

5 Claims, 9 Drawing Sheets

(56) References Cited

U.S. PATENT DOCUMENTS

| | | | |
|---|---|---|---|
| 7,313,053 | B2 | 12/2007 | Wodnicki |
| 7,549,961 | B1 | 6/2009 | Hwang |
| 8,852,103 | B2 | 10/2014 | Rothberg et al. |
| 9,194,941 | B2 | 11/2015 | Hiriyannaiah |
| 9,229,097 | B2 | 1/2016 | Rothberg et al. |
| 9,327,142 | B2 | 5/2016 | Rothberg et al. |
| 9,351,706 | B2 | 5/2016 | Rothberg et al. |
| 9,492,144 | B1 | 11/2016 | Chen et al. |
| 10,859,687 | B2 | 12/2020 | Bao et al. |
| 2003/0097071 | A1 | 5/2003 | Halmann et al. |
| 2003/0125627 | A1 | 7/2003 | Gee |
| 2003/0204142 | A1 | 10/2003 | Brock-Fisher et al. |
| 2004/0000841 | A1 | 1/2004 | Phelps et al. |
| 2004/0066708 | A1* | 4/2004 | Ogawa ............... G01S 7/52046 367/138 |
| 2005/0033168 | A1* | 2/2005 | Shifrin ............... G01S 7/52017 600/437 |
| 2005/0058021 | A1 | 3/2005 | Feintuch et al. |
| 2005/0148840 | A1 | 7/2005 | Lazenby |
| 2006/0092930 | A1 | 5/2006 | Shah |
| 2006/0179201 | A1 | 8/2006 | Riedel et al. |
| 2007/0014190 | A1 | 1/2007 | Fehl et al. |
| 2007/0242567 | A1 | 10/2007 | Daft et al. |
| 2008/0264171 | A1* | 10/2008 | Wodnicki ............... A61B 8/00 73/618 |
| 2009/0048520 | A1 | 2/2009 | Marteau et al. |
| 2009/0250729 | A1 | 10/2009 | Lemmerhirt et al. |
| 2010/0152587 | A1 | 6/2010 | Haider et al. |
| 2010/0317972 | A1 | 12/2010 | Baumgartner et al. |
| 2011/0055447 | A1 | 3/2011 | Costa |
| 2011/0060225 | A1 | 3/2011 | Cogan |
| 2011/0074244 | A1 | 3/2011 | Osawa |
| 2011/0077520 | A1 | 3/2011 | Osawa |
| 2011/0101824 | A1 | 5/2011 | Nishigaki |
| 2013/0111278 | A1 | 5/2013 | Jan et al. |
| 2013/0178744 | A1 | 7/2013 | Kierulf et al. |
| 2013/0226002 | A1 | 8/2013 | Miyachi |
| 2014/0171797 | A1 | 6/2014 | Hershey et al. |
| 2014/0243614 | A1 | 8/2014 | Rothberg et al. |
| 2014/0243676 | A1* | 8/2014 | Cogan ............... G10K 11/346 600/459 |
| 2014/0249420 | A1* | 9/2014 | Akahane ............... A61B 8/54 600/459 |
| 2014/0288428 | A1 | 9/2014 | Rothberg et al. |
| 2014/0323871 | A1* | 10/2014 | Bardelli ............... A61B 8/5292 600/459 |
| 2015/0032002 | A1 | 1/2015 | Rothberg et al. |
| 2015/0092515 | A1 | 4/2015 | Hiriyannaiah |
| 2015/0297193 | A1 | 10/2015 | Rothberg et al. |
| 2015/0301165 | A1 | 10/2015 | Rothberg et al. |
| 2016/0202349 | A1 | 7/2016 | Rothberg et al. |
| 2016/0213258 | A1* | 7/2016 | Lashkari ............... A61B 5/0095 |
| 2016/0331353 | A1 | 11/2016 | Ralston et al. |
| 2017/0143306 | A1 | 5/2017 | Rothberg et al. |
| 2017/0285152 | A1 | 10/2017 | Bao et al. |
| 2019/0142391 | A1 | 5/2019 | Bao et al. |

FOREIGN PATENT DOCUMENTS

| | | |
|---|---|---|
| CN | 104067517 A | 9/2014 |
| CN | 105431749 A | 3/2016 |
| CN | 106461767 A | 2/2017 |
| JP | 2004-275265 A | 10/2004 |
| JP | 2008-022887 A | 2/2008 |
| JP | 2008-272471 A | 11/2008 |
| JP | 2009065399 A | 3/2009 |
| JP | 2010-162351 A | 7/2010 |
| JP | 2011-056258 A | 3/2011 |
| JP | 2014180362 A | 9/2014 |
| WO | WO 2009/135255 A1 | 11/2009 |
| WO | WO 2010/055427 A1 | 5/2010 |
| WO | WO 2015/048820 A1 | 4/2015 |
| WO | WO 2015/161157 A | 10/2015 |
| WO | WO 2016/057622 A1 | 4/2016 |
| WO | WO 2016/057631 A1 | 4/2016 |

OTHER PUBLICATIONS

Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., CMUT-in-CMOS ultrasonic transducer arrays with on-chip electronics. Transducers 2009. IEEE. Jun. 21, 2009;1222-5.

Cheng et al., Electrical Through-Wafer Interconnects with Sub-PicoFarad Parasitic Capacitance. 2001 Microelectromechan Syst Conf. Aug. 24, 2001;18-21.

Daft et al., 5F-3 A Matrix Transducer Design with Improved Image Quality and Acquisition Rate. 2007 IEEE Ultrasonics Symposium. Oct. 1, 2007;411-5.

Daft et al., Microfabricated Ultrasonic Transducers Monolithically Integrated with High Voltage Electronics. 2004 IEEE Ultrasonics Symposium. Aug. 23, 2004;1:493-6.

Gurun et al., Front-end CMOS electronics for monolithic integration with CMUT arrays: circuit design and initial experimental results. Proc Ultrason Symp. 2008;390-3.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.

Kim et al., Design and Test of a Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

International Search Report and Written Opinion dated Jun. 27, 2017 in connection with International Application No. PCT/US2017/025297.

International Search Report and Written Opinion dated Jun. 28, 2017 in connection with International Application No. PCT/US2017/025349.

International Search Report and Written Opinion dated Nov. 13, 2014 for Application No. PCT/US2014/032803.

International Preliminary Report on Patentability dated Oct. 11, 2018 in connection with Application No. PCT/US2017/025297.

International Preliminary Report on Patentability dated Oct. 11, 2018 in connection with Application No. PCT/US2017/025349.

Extended European Search Report dated Oct. 25, 2019 in connection with European Application No. 17776764.7.

Extended European Search Report dated Jan. 30, 2020 in connection with European Application No. 177766764.7.

EP 17776746.4, Nov. 2, 2020, European Communication.

European Communication dated Nov. 2, 2020 in connection with European Application No. 17 776 746.4.

\* cited by examiner

TRANSMIT GENERATOR FOR CONTROLLING A MULTILEVEL PULSER OF AN ULTRASOUND DEVICE, AND RELATED METHODS AND APPARATUS

BACKGROUND

Field

The present application relates to transmit generators in ultrasound devices, and related methods and apparatus.

Related Art

Some ultrasound devices include a waveform generator which provides electric waveforms to a pulser. In response, the pulser controls an ultrasonic transducer to emit ultrasound acoustic waves.

BRIEF SUMMARY

According to an aspect of the present application, a method of operating an ultrasound device is provided, comprising generating a multi-level acoustic waveform with an ultrasound device by providing a series of data packets sequentially to a pulsing circuit coupled to an ultrasonic transducer of the ultrasound device.

According to an aspect of the present application, a method of controlling a plurality of pulsers coupled to a plurality of ultrasonic transducers is provided, comprising: transmitting a first packet to at least one pulser of the plurality of pulsers, the first packet comprising a first value representing a first reference voltage selected from a plurality of selectable reference voltages; providing a first control signal to represent a first duration of a first pulse segment; in response to transmitting the first packet to the at least one pulser of the plurality of pulsers, setting the at least one pulser of the plurality of pulsers to a first state corresponding to the first reference voltage throughout the first duration of the first pulse segment; transmitting a second packet to the at least one pulser of the plurality of pulsers, the second packet comprising a second value representing a second reference voltage selected from the plurality of selectable reference voltages; providing a second control signal to represent a second duration of a second pulse segment; and in response to transmitting the second packet to the at least one pulser of the plurality of pulsers, setting the pulser of the plurality of pulsers to a second state corresponding to the second reference voltage throughout the second duration of the second pulse segment, wherein the plurality of selectable reference voltages comprises at least three reference voltages.

According to an aspect of the present application, a method of controlling a plurality of pulsers coupled to a plurality of ultrasonic transducers is provided, the method comprising: selecting two or more waveform segments from among a plurality of waveform segments; concatenating the selected two or more waveform segments to form an input waveform; and providing the input waveform to a pulser of the plurality of pulsers coupled to the plurality of ultrasonic transducers.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1A:
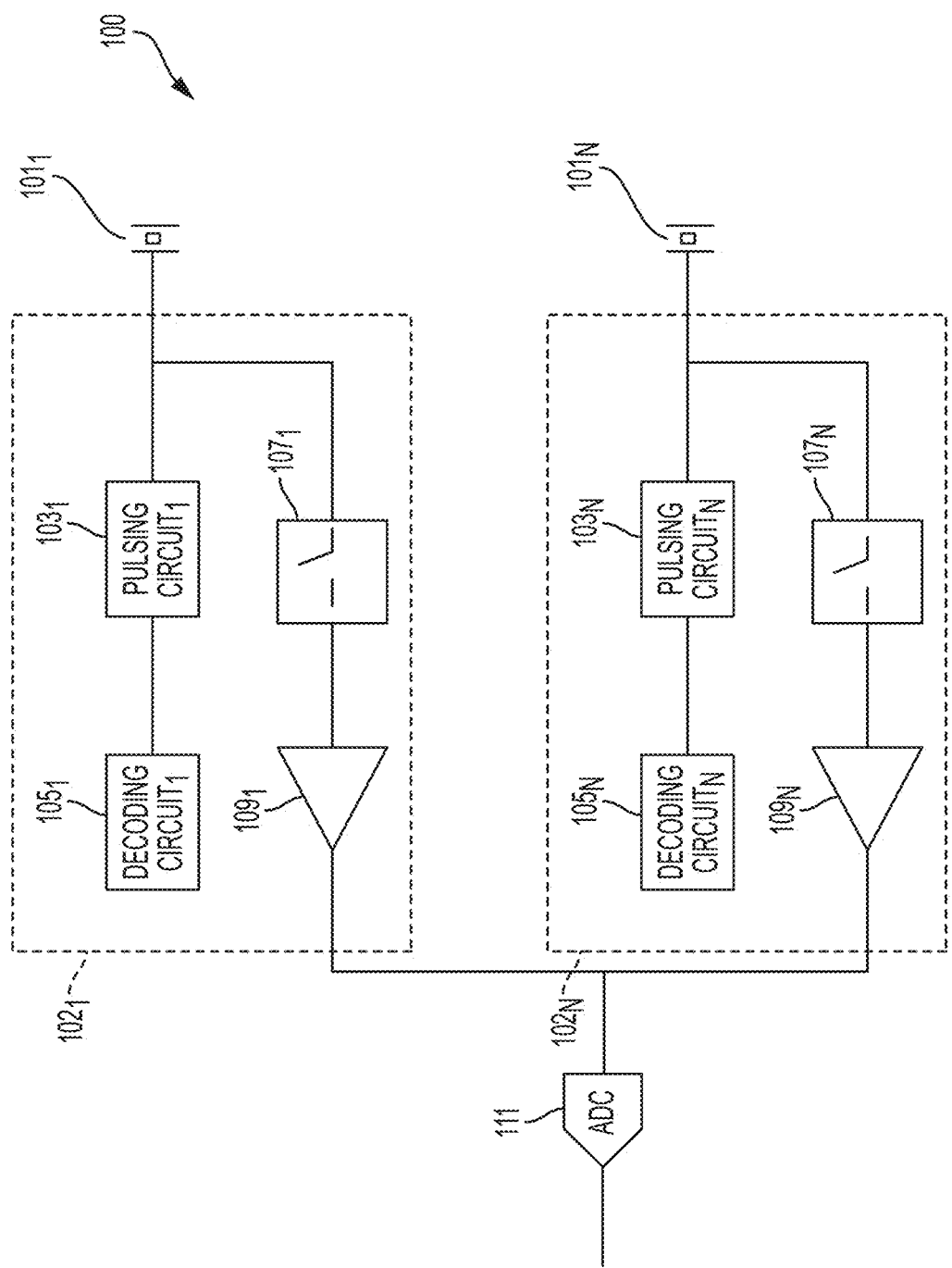
FIG. 1A illustrates schematically a block diagram of an ultrasound device comprising a plurality of pulsing circuits and a plurality of decoding circuits, according to a non-limiting embodiment of the present application.

An ultrasound probe may include integrated circuitry for generating waveforms emitted by the probe. The integrated circuitry may be fabricated on a complementary metal oxide semiconductor (CMOS) die, also referred to herein as a "chip." In some embodiments, ultrasonic transducers may be integrated with the CMOS chip, thus forming an ultrasound-on-a-chip device. For example, the ultrasonic transducers may be capacitive micromachined ultrasonic transducers (CMUTs), which may be integrated with the integrated circuitry on the CMOS die. The integrated circuitry may include waveform generation circuitry configured to produce the electric waveforms which drive the ultrasonic transducers.

Aspects of the present application provide programmable waveform generators for controlling pulsers of an ultrasound device to create multi-level pulses. Applicant has appreciated that ultrasound devices configured to generate multi-level pulses may significantly enhance the contrast of the ultrasound images produced. According to one aspect of the present application, pulsing circuits designed to provide multi-level pulses are used to facilitate the formation of temporal and spatial apodization. Apodization may reduce the extent of the side-lobes associated with transmitted pulses, thus increasing the resolution of the image produced. Multi-level pulses of the type described herein can assume any value selected from among a set of selectable values, where the set may comprise at least three values.

The generation of such multi-level pulses may require complicated driving circuitry to control the state of the pulsing circuits. The complexity of the driving circuitry may be further exacerbated when the generation of the multi-level pulses occurs asynchronously. The complexity of the driving circuitry translates into sizable power and space requirements. This may be impractical when the ultrasound device is to be disposed in a handheld ultrasound probe, stethoscope, or other compact form, in which the available power may be limited (e.g., to the power that can be supplied by batteries) or the power consumption kept below some threshold to prevent overheating or unsafe operation, and the real estate may be limited to a few cubic centimeters.

Applicant has appreciated that multi-level pulses may be generated using software-defined waveform generators. Software-defined waveform generators of the type described herein may significantly reduce the power and space requirements of the waveform generator(s) by limiting the amount of hardware used to perform pulse generation. The waveform generator may have access to a memory storing templates, such that each template represents a specific state for the pulsing circuits. For example, the templates may contain a set of selectable referenced voltages that a pulsing circuit can lock to. The templates may also be referred to herein as "master segments," "waveform segments," or by other similar terminology. The waveform generator may comprise a controller configured to access the templates stored in the memory, and packetize templates such that each packet may control one or more pulsing circuits to generate a pulse segments. "Pulse segments" will be referred to herein as pulse portions, such that the voltage of the pulse is constant throughout the duration of the pulse segment, and is locked to the selected reference voltage. As will be described further below, master segments and packets are defined in the digital domain while pulse segments are defined in the analog domain.

According to another aspect of the present application, spatial apodization of ultrasound signals is achieved using circuitry which operates on a serial data stream input provided by a waveform generator, rather than parallel input data streams. In some embodiments, decoding circuitry disposed along the packet data path between the waveform generator and the pulsing circuits of an ultrasound device may be configured to provide spatial apodization by receiving and spatially modulating the packets generated by the waveform generator based on a desired spatial profile. Accordingly, each ultrasonic transducer of the array may be provided with an input control value that depends on the location of the transducer. The use of decoding circuitry of the type described herein significantly simplifies the design of the waveform generator, which can be configured to generate serialized streams of packets.

These features may facilitate formation of a power and space-efficient circuit for generating waveforms to control ultrasonic transducers, and thus may facilitate formation of an ultrasound-on-a-chip device including a CMOS substrate with integrated circuitry and ultrasonic transducers.

The aspects and embodiments described above, as well as additional aspects and embodiments, are described further below. These aspects and/or embodiments may be used individually, all together, or in any combination of two or more, as the application is not limited in this respect.

According to one aspect of the present application, pulsing circuits configured to provide multi-level pulses are provided. The pulsing circuits may be configured to provide one or more pulses to a respective ultrasonic transducer of an ultrasound device. The pulse(s) may be formed by a succession of pulse segments. Each pulse segment of the pulse may assume one among a set of selectable reference voltages, between an initial time $t_i$ and a final $t_f$. The pulses may be asynchronous in some embodiments, such that the duration $t_f$-$t_i$ of each pulse segment may be variable.

FIG. 1A illustrates schematically a block diagram of an ultrasound device comprising a plurality of pulsing circuits and a plurality of decoding circuits, according to a non-limiting embodiment of the present application. Ultrasound device 100 may comprise a plurality of circuitry channels $102_1 \ldots 102_N$, where N is an integer. Circuitry channels $102_1 \ldots 102_N$ may be electrically connected to respective ultrasonic transducers $101_1 \ldots 101_N$. Ultrasound device 100 may further comprise analog-to-digital converter (ADC) 111.

The circuitry channels $102_1 \ldots 102_N$ may comprise circuitry for the transmission and/or reception of ultrasound acoustic waves. On the transmitter side, circuitry channels $102_1 \ldots 102_N$ may comprise decoding circuits $105_1 \ldots 105_N$ coupled to respective pulsing circuits $103_1 \ldots 103_N$. The pulsing circuits $103_1 \ldots 103_N$ may control respective ultrasonic transducers $101_1 \ldots 101_N$ to emit acoustic waveforms.

Pulsing circuits $103_1 \ldots 103_N$ are circuits, in some embodiments, configured to provide pulses to respective ultrasonic transducers $101_1 \ldots 101_N$. In some embodiments, pulsing circuits $103_1 \ldots 103_N$ may provide multi-level pulses exhibiting three or more levels selected from a set of selectable levels. The selectable levels may be reference voltages in some embodiments. The pulsing circuits may be configured to receive one reference voltage at a time and to form pulses that lock to the received reference voltage. In some embodiments, the pulsers may provide bipolar pulses capable of exhibiting positive and/or negative voltages.

Figure 1B:
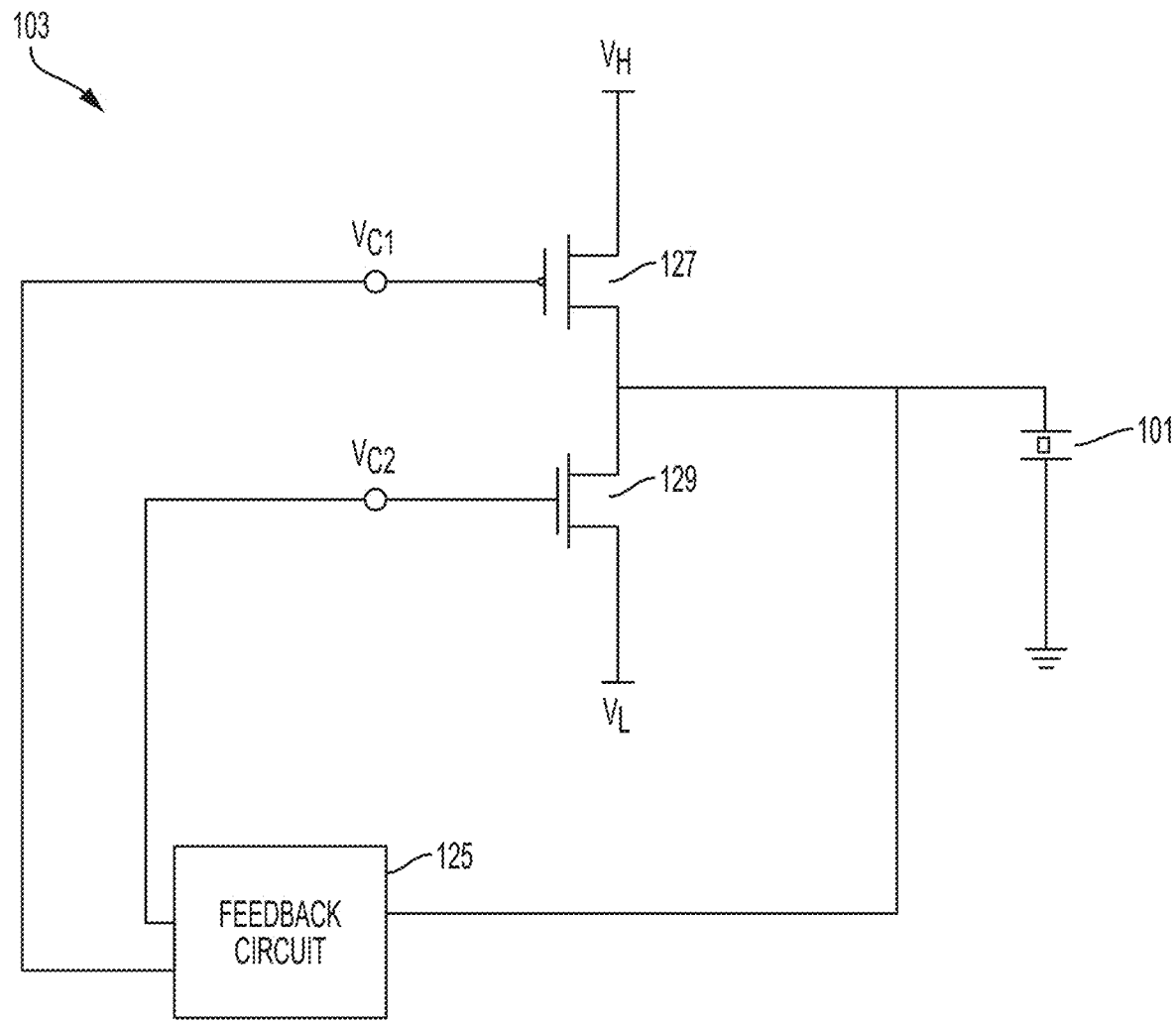
FIG. 1B illustrates a circuit diagram of a pulsing circuit comprising two transistors, according to one aspect of the present application.

In some embodiments, pulsing circuits $103_1 \ldots 103_N$ may comprise two transistors. FIG. 1B illustrates a circuit diagram of a pulsing circuit 103 which may serve as any of the pulsing circuits $103_1 \ldots 103_N$ of FIG. 1A. The pulsing circuit 103 of FIG. 1B comprising a first transistor 127 and a second transistor 129. In some embodiments, transistor 127 is a positive metal-oxide-semiconductor (pMOS) transistor and transistor 129 is a negative metal-oxide-semiconductor (nMOS) transistor. However, any other suitable number and/or type of transistor may be used.

Transistor 127 may be set to a conductive state through control signal $V_{c1}$ when a new reference voltage, greater than the previously selected reference voltage, is selected. In this case, transistor 127 may drive an electric current between supply voltage $V_H$ and ultrasonic transducer 101 and the voltage across the terminals of the ultrasonic transducer may be increased until the currently selected reference voltage is reached. A feedback circuit 125 may compare the voltage across the terminals of the ultrasonic transducer and compare it to the currently selected reference voltage. When the voltage across the terminals of the transducer is equal to the reference voltage, or alternatively, is equal to a voltage proportional to the reference voltage by a constant and predefined factor, feedback circuit 125 may turn off transistor 127 through control signal $V_{c1}$. Owing to the fact that ultrasonic transducer 101 is capacitive, the ultrasonic transducer may hold a voltage across its terminals that is equal or proportional to the reference voltage.

Similarly, transistor 129 may be set to a conductive state through control signal $V_{c2}$ when a new reference voltage, less than the previously selected reference voltage, is selected. In this case, transistor 129 may drive an electric current between supply voltage $V_L$ and ultrasonic transducer 101, and the voltage across the terminals of the ultrasonic transducer may be decreased until the currently selected reference voltage is reached. In some embodiments, $V_L$ is less than $V_H$. $V_L$ may be a positive voltage, a negative voltage, or zero. Feedback circuit 125 may compare the voltage across the terminals of the ultrasonic transducer to the currently selected reference voltage. When the voltage across the terminals of the transducer is equal to the reference voltage, or alternatively, is equal to a voltage proportional to the reference voltage by a constant and predefined factor, feedback circuit 125 may turn off transistor 129 through control signal $V_{c2}$. Owing to the fact that ultrasonic transducer 101 is capacitive, the transducer may hold a voltage across its terminals that is equal or proportional to the reference voltage.

Aspects of the present application provide decoding circuits suitable for use in an ultrasound device having a plurality of multi-level pulsers. An example relates to decoding circuits $105_1 \ldots 105_N$ of FIG. 1A. In some embodiments, decoding circuits $105_1 \ldots 105_N$ may be part of a single circuitry element, while in other embodiments, they may comprise separate circuits. In some embodiments, each decoding circuit may correspond to a respective ultrasonic transducer. However, in other embodiments, more than one ultrasonic transducer may share one decoding circuit. In some embodiments, decoding circuits $105_1 \ldots 105_N$ may be configured to modulate the packets, as described further below, generated by a waveform generator and to provide the modulated packets to respective pulsing circuits $103_1 \ldots 103_N$. In some embodiments, decoding circuits $105_1 \ldots 105_N$ may provide pulses to respective pulsing circuits $103_1 \ldots 103_N$ such that spatial apodization is obtained.

As will be described further below, ultrasound device 100 may further comprise one or more waveform generators (not shown in FIG. 1A) configured to provide serialized packets to decoding circuits $105_1 \ldots 105_N$. In some embodiments, the waveform generator(s) may be configured to form packets by aggregating master segments selectable from a library of selectable master segments.

Referring back to FIG. 1A, the receive circuitry of the circuitry channels $102_1 \ldots 102_N$ may receive the electrical signals from respective ultrasonic transducers $101_1 \ldots 101_N$ in response to receiving an ultrasound acoustic wave. In the illustrated example, each circuitry channel $102_1 \ldots 102_N$ comprises a respective receive switch $107_1 \ldots 107_N$ and a receiving circuit $109_1 \ldots 109_N$. The receive switches $107_1 \ldots 107_N$ may be controlled to activate/deactivate readout of an electrical signal from a given ultrasonic transducer $101_1 \ldots 101_N$. In some embodiments, the receiving circuits $109_1 \ldots 109_N$ may comprise trans-impedance amplifiers (TIAs).

Ultrasound device 100 may further comprise ADC 111. ADC 111 may be configured to digitize the signals received by ultrasonic transducers $101_1 \ldots 101_N$. The digitization of the various received signals may be performed in series or in parallel.

While FIG. 1A illustrates a number of components as part of a circuit of an ultrasound device, it should be appreciated that the various aspects described herein are not limited to the exact components or configuration of components illustrated.

The ultrasonic transducers $101_1 \ldots 101_N$ are sensors, in some embodiments, producing electrical signals representing received ultrasound acoustic waves. The ultrasonic transducers may also transmit ultrasound acoustic waves in some embodiments. The ultrasonic transducers may be capacitive micromachined ultrasonic transducers (CMUTs) in some embodiments. However, other types of capacitive ultrasonic transducers may be used in other embodiments.

The components of FIG. 1A may be located on a single substrate or on different substrates. For example, the ultrasonic transducers $101_1 \ldots 101_N$ may be on a first substrate and the remaining illustrated components may be on a second substrate. The first and/or second substrates may be semiconductor substrates, such as silicon substrates. In an alternative embodiment, the components of FIG. 1A may be on a single substrate. For example, the ultrasonic transducers $101_1 \ldots 101_N$ and the illustrated circuitry may be monolithically integrated on the same semiconductor die.

According to an embodiment, the components of FIG. 1A form part of an ultrasound probe. The ultrasound probe may be handheld. In some embodiments, the components of FIG. 1A form part of an ultrasound patch configured to be worn by a patient.

Figure 1C:
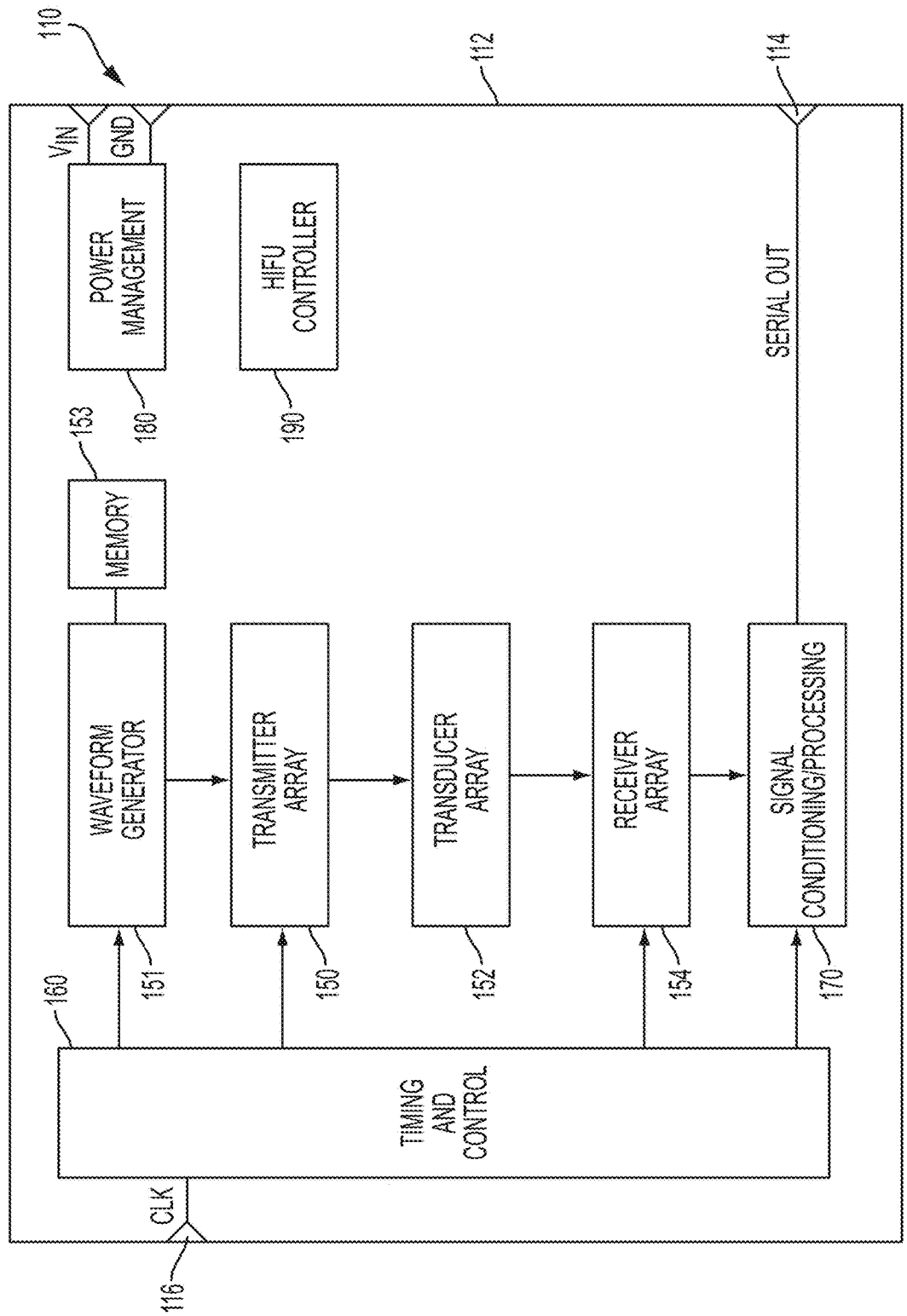
FIG. 1C illustrates schematically a block diagram of an ultrasound device comprising a waveform generator, according to some non-limiting embodiments.

As discussed above, the ultrasound device may comprise one or more waveform generators configured to generate a plurality of packets based on a set of selectable templates. The packets may be decoded by decoding circuits $105_1 \ldots 105_N$ and may be used to form multi-level pulses through pulsing circuits $103_1 \ldots 103_N$. FIG. 1C illustrates schematically a block diagram of an ultrasound device 110 comprising a waveform generator 151, according to some non-limiting embodiments. Ultrasound device 100 may further comprise memory 153, transmitter array 150, transducer array 152, receiver array 154, signal conditioning/processing circuit 170, timing and control circuit 160, power management circuit 180, or any suitable combination thereof.

In some embodiments, ultrasound device 110 may comprise some or all of the components of ultrasound device 100. Transmitter array 150 of ultrasound device 110 may comprise pulsing circuits $103_1 \ldots 103_N$ and decoding circuits $105_1 \ldots 105_N$ of ultrasound device 100 in some embodiments. Transducer array 152 may comprise ultrasonic transducers $101_1 \ldots 101_N$ in some embodiments. The ultrasonic transducers may be organized in one-dimensional or two-dimensional arrays. Receiver array 154 may comprise receive switches $107_1 \ldots 107_N$ and a receiving circuits $109_1 \ldots 109_N$ in some embodiments. Signal conditioning/processing unit 170 may comprise ADC 111. In some embodiments, signal conditioning/processing unit 170 may further comprise digital circuitry configured to form images based on the ultrasound acoustic waves received by transducer array 152.

According to aspects of the present application, waveform generator 151 may be configured to generate control signals to drive pulsing circuits $103_1 \ldots 103_N$ of transmitter array 150. The control signals may be organized in packets, such that each packet may comprise information corresponding to a selected reference voltage. In some embodiments, the packets may be directed to respective feedback circuits 125 of pulsing circuits $103_1 \ldots 103_N$. The content of the packets will be described in connection with FIG. 3A.

In some embodiments, waveform generator 151 may be connected to memory 153. As will be described further below, memory 153 may store a plurality of master segments. Waveform generator 151 may access memory 153 to obtain one or more master segments. Waveform generator 151 may combine various master segments to form a desired succession of packets.

In some embodiments, memory 153 may comprise random access memory (RAM) units, read-only memory (ROM) units, flash memory units, or any suitable type of memory that can store waveform segments. In some embodiments, waveform generator 151 may comprise one or more logic circuits. The logic circuit(s) may comprise processors, field-programmable gate arrays (FPGAs), application-specific integrated circuits (ASICs), microcontrollers, or any suitable combination thereof. Waveform generator 151 may be configured to access data stored in memory 153 and to execute computer instruction(s) to process the data obtained from the memory.

The ultrasound device 100 may further comprise an output port 114 which may be a physical interface between ultrasound device 100 and an external device. For example, output port 114 may connect to external devices capable of receiving and processing large amounts of ultrasound data, such as a specialized FPGA, a GPU, or other suitable device. While only a single output port 114 is illustrated, it should be appreciated that multiple output ports may be provided. Ultrasound device 100 may also include a clock input port 116 to receive and provide a clock signal CLK to the timing and control circuit 160.

Power management circuit 180 may receive ground (GND) and voltage reference ($V_{IN}$) signals. Optionally, a high-intensity focused ultrasound (HIFU) controller 190 may be included if ultrasound device 100 is to be used to provide HIFU. In the embodiment shown, all of the illustrated elements may be formed on a single semiconductor die (or substrate or chip) 112, though not all embodiments are limited in this respect.

Figure 2A:
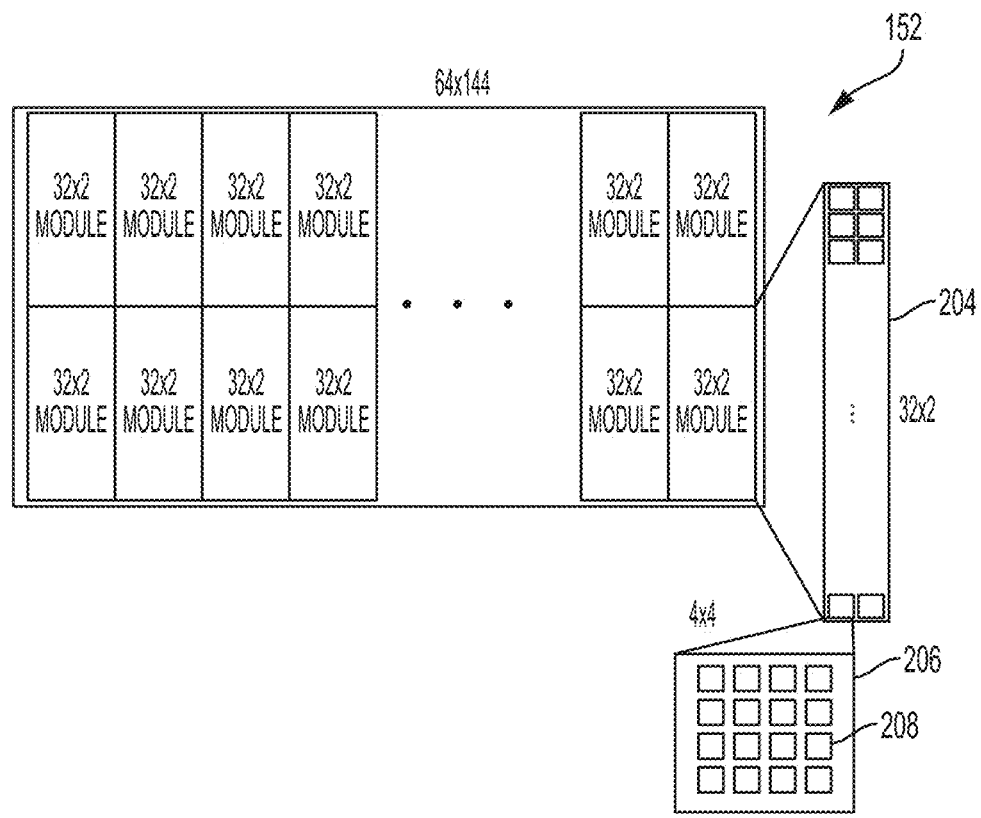
FIG. 2A shows an illustrative arrangement of a transducer array, according to a non-limiting embodiment of the present application.

Transducer array 152 may be arranged in rows and columns in some embodiments. FIG. 2A shows an illustrative arrangement of a transducer array, according to a non-limiting embodiments of the present application. As illustrated, transducer array 152 of an ultrasound device 100 may have multiple modules 204. As shown, a module 204 may comprise multiple elements 206. An element 206 may comprise multiple cells 208. A cell 208 may comprise an ultrasonic transducer of the type described in connection with FIG. 1A.

In the illustrated embodiment, transducer array 152 comprises 144 modules arranged as an array having 72 rows and 2 columns. However, it should be appreciated that a transducer array may comprise any suitable number of modules (e.g., at least one module, at least two modules, at least ten modules, at least 100 modules, at least 1000 modules, at least 5000 modules, at least 10,000 modules, at least 25,000 modules, at least 50,000 modules, at least 100,000 modules, at least 250,000 modules, at least 500,000 modules, between two and a million modules, or any number of range of numbers within such ranges) that may be arranged as a one-dimensional or two-dimensional array of modules having any suitable number of rows and columns or in any other suitable way.

In the illustrated embodiment, each module comprises 64 ultrasound elements arranged as an array having two rows and 32 columns. However, it should be appreciated that a module may comprise any suitable number of ultrasound elements (e.g., one element, at least two ultrasound elements, at least four ultrasound elements, at least eight ultrasound elements, at least 16 ultrasound elements, at least 32 ultrasound elements, at least 64 ultrasound elements, at least 128 ultrasound elements, at least 256 ultrasound elements, at least 512 ultrasound elements, between two and 1024 ultrasound elements, at least 2500 ultrasound elements, at least 5,000 ultrasound elements, at least 10,000 ultrasound elements, at least 20,000 ultrasound elements, between 1000 and 20,000 ultrasound elements, or any number of range of numbers within such ranges) that may be arranged as a one-dimensional or two-dimensional array of ultrasound elements having any suitable number of rows and columns or in any other suitable way.

In the illustrated embodiment, each ultrasound element comprises 16 cells 208 arranged as a two-dimensional array having four rows and four columns, a cell representing an ultrasonic transducer and those two terms being used synonymously herein. However, it should be appreciated that an element may comprise any suitable number of cells (e.g., one, at least two, at least four, at least 16, at least 25, at least 36, at least 49, at least 64, at least 81, at least 100, between one and 200, or any number or range of numbers within such ranges) that may be arranged as a one-dimensional or two dimensional array having any suitable number of rows and columns (square or rectangular) or in any other suitable way. In some embodiments, each cell 208 may comprise an ultrasonic transducer of the type described in connection with FIG. 1A.

In some embodiments, transmitter array 150 may be arranged in a configuration that matches the modules, ultrasound elements and cells illustrated in FIG. 2A, such that to each ultrasonic transducer correspond one pulsing circuit. However, other configurations are also possible. For example, a single pulsing circuit may be configured to drive a plurality of ultrasonic transducers, such as all the ultrasonic transducers of a cell 208.

According to one aspect of the present application, the circuitry used to generate multi-level pulses may be reduced, in some instances significantly, by performing the generation of the pulses via software. For example, a computer code may be programmed by a user to provide a desired pulse profile. The profile of the pulse may be engineered based on the nature of the target being probed and/or the environment in which the probing takes place. The computer code may comprise a set of instructions configured to interact with waveform generator 151. In response to the execution of the instructions, waveform generator 151 may generate a plurality of packets of the type described above.

Figure 2B:
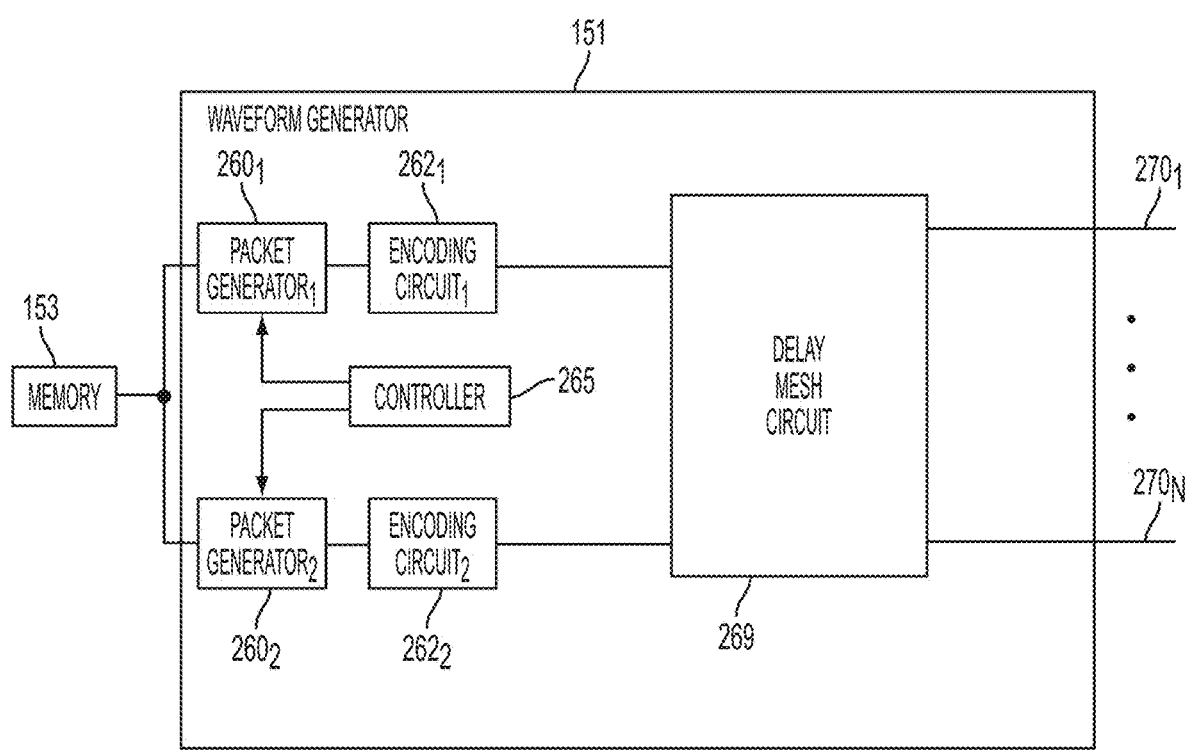
FIG. 2B illustrates schematically a block diagram of a waveform generator comprising a a plurality of packet generators, according to a non-limiting embodiment of the present application.

In some embodiments, waveform generator 151 may be configured to generate packets in a serialized fashion. Accordingly, each packet may be transmitted following the transmission of a preceding packet. However the application is not limited in this respect and packets may be transmitted using any suitable degree of parallelization. FIG. 2B illustrates schematically a block diagram of a waveform generator, according to a non-limiting embodiments of the present application. Waveform generator 151 may comprise one or more packet generators (e.g., packet generators $260_1$ and $260_2$), one or more encoding circuits (e.g., encoding circuits $262_1$ and $262_2$), controller 265 and delay mesh circuit 269.

Memory 153 may comprise a plurality of records, such that a record, and in some embodiments each record, contains one master segment. In some embodiments, the master segments collectively represent all the possible states that the pulsing circuits can assume. For example, the master segments may comprise a field for the selectable reference voltages. In some embodiments, the master segments may comprise a field for control signals $V_{c1}$ and $V_{c2}$ for respective feedback circuits 125 of pulsing circuits $103_1 \ldots 103_N$. In some embodiments, memory 153 may be partitioned, and may comprise at least one section for each packet generator. In such embodiments, packet generator $260_1$ may use data stored in a section of memory 153 and packet generator $260_2$ may use data stored in another section of memory 153. In some embodiments, such portions may overlap. In other embodiments, such portions may comprise the same portion.

In response to the execution of a set of computer instructions, controller 265 may control a packet generator to access memory 153 and to select a number of master segments, as requested by the user. The packet generator may form a succession of packets based on the selected master segment. Each packet may correspond to a selected master segment. In some embodiments, specific packets that do not have any corresponding master segment may be included in the packet stream by the packet generators. For example, the first packet of a succession of packets, or start_packet, may be generated by the packet generator before any other packet corresponding to a master segment. Additionally, or alternatively, the last packet of a succession of packets, or end_packet, may be generated by the packet generator after all other packets.

As illustrated in FIG. 2B, waveform generator 151 may comprise two packet generators, such that each packet generator provides packets to a column comprising a plurality of ultrasound elements (such as ultrasound element 206). However the application is not limited in this respect and any other suitable number of packet generators may be used such that each packet generator may provide packets to any suitable number of elements.

The packets generated by packet generators $260_1$ and $260_2$ may be provided to respective encoding circuits $262_1$ and $262_2$. In response, the encoding circuit may encode the packets provided. In some embodiments, encoding circuit may be configured to perform serialization of the packets. The encoding circuit may reduce the amount of data used to provide packets generated by the packet generator to the pulsing circuits, and thus may provide a valuable reduction in the amount of memory used to store and communicate the desired packets.

In some embodiments, the encoding circuit may be configured to implement an N-to-M bit encoder (where each of N and M is a positive integer and where N is greater than M) so that when the encoding circuit encodes an input signal consisting of B bits the resultant encoded signal includes approximately B*M/N bits (where B is a positive integer). As a specific non-limiting example, the encoding circuit may be configured to implement a 2-to-1 bit encoder so that when the encoding circuitry encodes an input signal of B bits, the resultant encoded signal has approximately B/2 bits. As another specific non-limiting example, the encoding circuitry may be configured to implement a 3-to-2 bit encoder so that when the encoding circuitry encodes an input signal of B bits, the resultant encoded signal has approximately 2B/3 bits. As yet another specific non-limiting example, the encoding circuitry may be configured to implement a 3-to-1 bit encoder so that when the encoding circuitry encodes an input signal of B bits, the resultant signal has approximately B/3 bits. More details of a non-limiting suitable encoding circuit may be found in U.S. Pat. No. 9,229,097, which is incorporated herein by reference in its entirety.

The encoded packets generated by encoding circuits $262_1$ and $262_2$ may be provided to delay mesh circuit 269 in some embodiments. Delay mesh circuit 269 may include a delay mesh for producing multiple versions of the packets, the delay mesh having an input configured to receive the packets generated by the waveform generator and a plurality of (parallel) outputs configured to provide the multiple versions of the packets to the plurality of pulsing circuits. The delay mesh may be controlled to produce different versions of the packets generated by the waveform generator in response to different controls applied to the delay mesh. In this way, the ultrasound device can be controlled to generate different types of ultrasound waveforms.

In some embodiments, delay mesh circuit 269 may comprise a plurality of delay mesh units each of which may delay packets to obtain one or more time-delayed versions of the packets and provide them as output signals to one or more pulsing circuits. Output signals provided to one or more other delay mesh units may be further time-delayed by those delay mesh units and be transmitted and/or further processed by still other delay mesh units. In this way, a packet input to the delay mesh circuit may propagate through a plurality of delay mesh units, with one or more of the delay mesh units time-delaying the packet providing the resulting time-delayed version(s) to one or more ultrasound elements for transmission. As such, delay mesh circuitry may generate multiple time-delayed versions of the packet and provide these versions the pulsing circuits. A delay mesh unit may comprise a buffer for storing and/or performing operations on a packet. In some embodiments, delay mesh circuit 269 may comprise many delay mesh units and, as such, reducing the size of the buffer of each delay mesh unit may reduce both space and power requirements of implementing delay mesh circuitry on a single substrate ultrasound device. More details of a non-limiting suitable delay mesh circuit may be found in U.S. Pat. No. 9,229,097, which is incorporated herein by reference in its entirety.

In some embodiments, delay mesh circuit 269 may have a plurality of outputs $270_1 \ldots 270_N$. In some embodiments, the number of output is equal to the number of pulsing circuits of transmitter array 150. The various outputs $270_1 \ldots 270_N$ may be different time-delayed versions of the packets provided by the encoding circuits in some embodiments. In other embodiments, the various outputs $270_1 \ldots 270_N$ may all have equal delays. In some embodiments, delay mesh circuit 269 may be configured to provide temporal apodization.

Figure 2C:
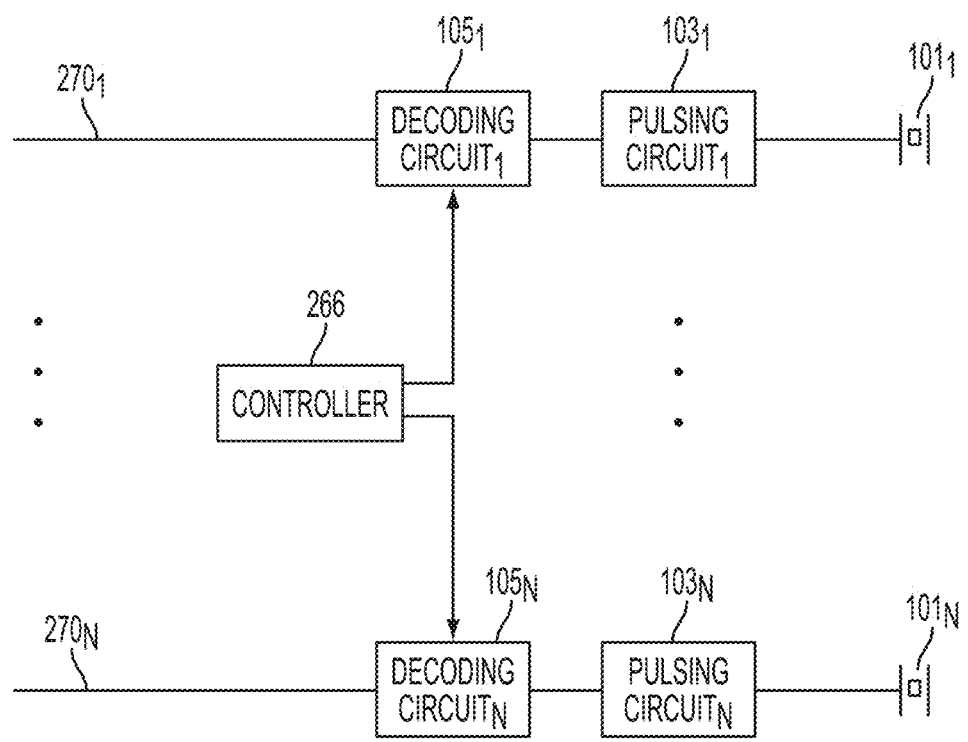
FIG. 2C illustrates schematically a block diagram of an ultrasound device comprising a plurality of decoding circuits, according to a non-limiting embodiment of the present application.

According to aspects of the present application, transmitter array 150 may comprise a plurality of decoding circuits. In some embodiments, the encoding circuits may decode the packets obtained through outputs $270_1 \ldots 270_N$. FIG. 2C illustrates schematically a block diagram of an ultrasound device comprising a plurality of decoding circuits, according to a non-limiting embodiments of the present application. Each decoding circuit $105_1 \ldots 105_N$ may receive one or more packets from respective outputs $270_1 \ldots 270_N$. Controller 266 may be configured to control the decoding circuits $105_1 \ldots 105_N$. While the decoding circuits are shown as separate elements, they may be part of a single decoder circuit block in some embodiments. Each decoding circuit may be connected to a respective pulsing circuit $103_1 \ldots 103_N$. Each pulsing circuit may be connected to a ultrasonic transducer $101_1 \ldots 101_N$.

In some embodiments, controller 266 may operate in response to the execution of a set of computer instructions. In some embodiments, decoding the serialized packet may comprise performing a serial-to-parallel conversion. Accordingly, the decoding circuits may receive the packet one bit at a time, and may form one or more words of bits. For example, one word may comprise the bits used to define a reference voltage. In some embodiments, the word corresponding to the reference voltage may be transmitted in parallel by the encoding circuits to respective pulsing circuits. "Parallel transmission" will be referred to herein such that each bit forming a word is transmitted on a respective conductive wire.

In some embodiments, controller 266 may be configured to modulate the packets received. "Modulation" of a packet as used herein refers to the multiplication, or division, of the value of the packet corresponding to the selected reference voltage by a desired factor. The effect of modulating a packet is the generation of a scaled version of the reference voltage transmitted within the packet. In some embodiments, the various packets received by the decoding circuits may be modulated with different factors. For example, the packets may be modulated according to a desired modulation profile, such that each decoding circuit may provide a desired factor.

Packets may be modulated to provide spatial apodization across the array of ultrasonic transducers. In some embodiments, the reference voltage contained in a packet may be modulated by dividing, or multiplying it by a factor that is between 0.001 and 1 in some embodiments, between 0.001 and 0.999 in some embodiments, between 0.01 and 0.99 in some embodiments, between 0.1 and 0.9 in some embodiments, between 0.25 and 0.75 in some embodiments, between 0.4 and 0.7 in some embodiments, or between any other suitable values or range of values. Other values are also possible. In some embodiments the modulation may be performed in the digital domain. In some embodiments, the modulation factors may be represented by two bits, thus providing four combinations. By way of example and not limitation, the modulation factors may be equal to 0, 0.4, 0.7 and 1. Other values are also possible. As the decoding circuits receive packets, the corresponding reference voltages may be multiplied by one of the four modulation factors described herein. By way of example and not limitation, the decoding circuits may be configured to perform spatial apodization, such that the emitted ultrasound acoustic wave has a main lobe in the middle of the array and the intensity decays toward the edges of the array.

In some embodiments, the decoding circuits may be configured to implement an M-to-N bit decoder (where each of N and M is a positive integer and where N is greater than M) so that when the decoding circuits decode an input signal of B bits the resultant decoded signal has approximately B*N/M bits (where B is a positive integer). As a specific non-limiting example, a decoding circuit may be configured to implement a 1-to-2 bit decoder so that when the decoding circuitry decodes an input signal of B bits, the resultant decoded signal has approximately 2B bits. The decoding function may be the inverse of the encoding function provided by encoding circuits $262_1$ and $262_2$.

Figure 3A:
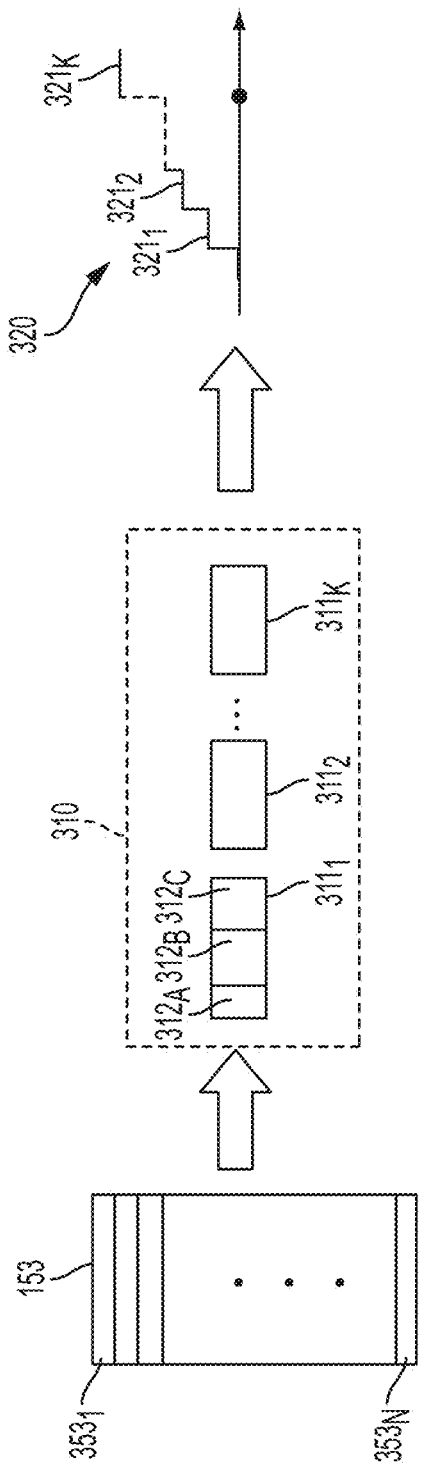
FIG. 3A illustrates a data path diagram showing a succession of packets, according to a non-limiting embodiment of the present application.

FIG. 3A illustrates a data path diagram showing a succession of packets, according to a non-limiting embodiment of the present application. FIG. 3A illustrates memory 153 comprising a plurality of records, such that each record contains a master segment $353_1 \ldots 353_N$. As described above, master segments $353_1 \ldots 353_N$ collectively represent a base for the generation of desired pulse profiles. Stage 310 of the data path represents the generation of an non-limiting exemplary succession of packets $311_1, 311_2 \ldots 311_k$ where k may assume any integer value greater than two. Each packet may correspond to one of the master segments. The succession of packets may begin with a start_packet and/or may end with an end_packet.

Packet $311_1$ is shown in additional detail. In some embodiments, packet $311_1$ may comprise a field $312_A$ containing one or more bits to determine the conductive state of transistors 127 and 129. Field $312_A$ may be directed to a feedback circuit 125 of a respective pulsing circuit. Based on field $312_A$, the feedback circuit may control signals $V_{c1}$ and $V_{c2}$.

In some embodiments, packet $311_1$ may comprise a field $312_B$ containing one or more bits representing a reference voltage. The number of bits needed to represent the reference voltage may depend on the number of selectable reference voltages. As an example, if n is the number of selectable voltages, field $312_E$ may contain a number of bits that is greater than, less than, or equal to $\log_2 n$. In some embodiments, the number of bits used to represent field $312_E$ may be reconfigured during run-time. For example, the multi-level pulser may be reconfigured, during run-time, to operate as a 2-level pulser. In such circumstance, the number of bits representing the reference voltage may be reduced. Field $312_E$ may be directed to a feedback circuit 125 of a respective pulsing circuit. In some embodiments, packet $311_1$ may comprise a field $312_C$ containing one or more control bits. The control bits may be directed to delay mesh circuit 269 to determine the delays across output $270_1 \ldots 270_N$ and/or to controller 266 to control the spatial apodization profile.

The succession of packets may be used by a pulsing circuit to generate a pulse 320, as illustrated in FIG. 3A. Pulse 320 may comprise pulse segments $321_1, 321_2 \ldots 321_k$, such that each pulse segment is generated in response to a respective packet $311_1, 311_2 \ldots 311_k$. The duration of each pulse segment may be controlled by a counter configured to count clock cycles until a predetermined segment duration is reached. The pulse may be asynchronous in some embodiments, such that pulse segments may have different durations. As illustrated, the master segments and the packets may be defined in the digital domain while the pulse segments may be defined in the analog domain.

Figure 3B:
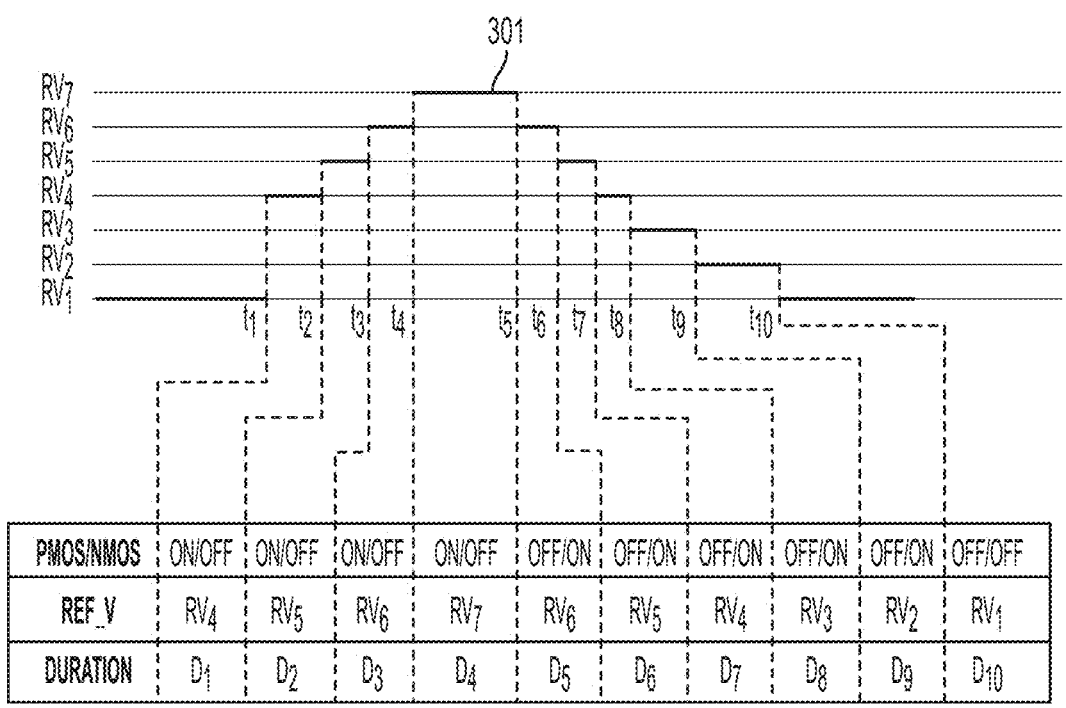
FIG. 3B illustrates a time diagram showing an exemplary multi-level pulse formed through a succession of packets, according to a non-limiting embodiment of the present application.

FIG. 3B illustrates a time diagram showing an exemplary multi-level pulse 301 formed through a succession of packets, according to a non-limiting embodiment of the present application. In the example shown, a reference voltage may be selected from among seven selectable reference voltages $RV_1 \ldots RV_7$. At times $t_1, t_2, t_3, t_4, t_5, t_6, t_7, t_8, t_9$ and $t_{10}$ a new reference voltage is selected. For example, $RV_4$ is selected at $t_1$, $RV_5$ is selected at $t_2$, $RV_6$ is selected at $t_3$, etc. An "event" is defined herein as the time at which a new reference voltage is selected, such as time $t_1, t_2, t_3$, etc. While in the non-limiting example of FIG. 3B a set of seven selectable reference voltages are provided, any suitable number of reference voltages may be employed. In some embodiments, the pulse may be bipolar and each selectable reference voltage can be positive and/or negative.

In some embodiments, the packet may comprise field PMOS/NMOS, serving as field 312A. The pMOS transistor may be activated (ON state) to increase the voltage in response to the selection of a reference voltage that is greater than the reference voltage previously selected. The nMOS transistor may be activated (ON state) to decrease the voltage in response to the selection of a reference voltage that is less than the reference voltage previously selected. During a segment, and in some embodiments during each segment, at least one transistor is deactivated (OFF state). In some embodiments, the packet may comprise field REF_V, serving as field $312_B$ to select a reference voltage, from the set of selectable reference voltage. In the non-limiting example of FIG. 3B, which exhibits a set of seven selectable reference voltages, REF_V may comprise three or more bits to produce eight or more combinations. In some embodiments, a clock counter may count clock cycles until a duration associated with a packet is reached. In the embodiment shown in FIG. 3B, the packets exhibit respective durations $D_1, D_2, D_3, D_4, D_5, D_6, D_7, D_8, D_9$ and $D_{10}$ defined by the field duration.

Figure 4:
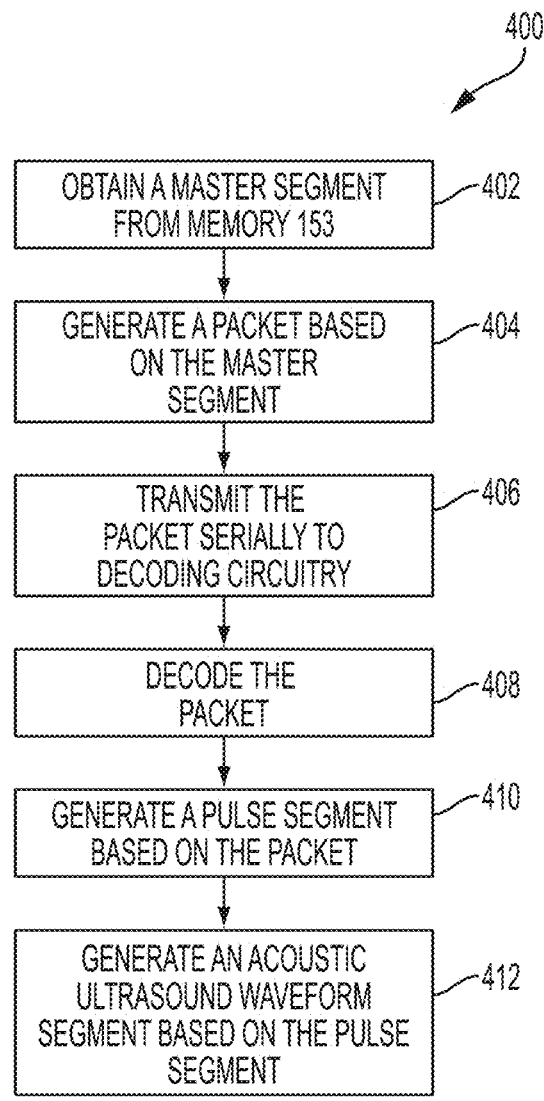
FIG. 4 illustrates a method of controlling a plurality of pulsers coupled to a plurality of ultrasonic transducers, according to a non-limiting embodiment of the present application.

FIG. 4 illustrates the steps of a method of controlling a plurality of pulsers coupled to a plurality of ultrasonic transducers, according to a non-limiting embodiment of the present application. Method 400 may begin at act 402, in which waveform generator 151 may access memory 153, and may obtain a master segment. This operation may be triggered by the execution of a computer code in some embodiments. The master segment may comprise values intended to define the characteristics of a corresponding pulse segment. For example, the master segment may comprise a value representing a reference voltage of a plurality of selectable reference voltages. In response, the corresponding pulse segment may have a voltage locked to the reference voltage. In some embodiments, the master segment may comprise a value representing the conductive state of a first transistor, such as transistor 127 and/or the conductive state of a second transistor, such as transistor 129. Based on such value, transistors 127 and 129 may be set to a conductive or a non-conductive state throughout the duration of the pulse segment corresponding to the master segment.

At act 404, waveform generator 151 may form a packet based on the master segment obtained from memory 153 at act 402. In some embodiments, the packet formed may comprise the one or more values defined in the master segment. In some embodiments, the packet may comprise values that may be used to control the data path of the packet. In some embodiments, the packet may comprise a value representing the duration of the pulse segment corresponding to the packet. In other embodiments, the duration of a pulse segment may be defined through a counter configured to count clock cycles until the desired number of clock cycles is reached.

At act 406, the packet may be transmitted to decoding circuitry. The decoding circuitry may comprise decoding circuits $105_1 \ldots 105_N$ in some embodiments. The packet may be transmitted serially. For example, the packet may be transmitted one bit at a time. In some embodiments, waveform generator 151 may comprise one or more packet generators, such as packet generators $260_1$ and $260_2$, each of which may transmit a packet serially.

In some embodiments, waveform generator 151 may obtain a plurality of master segments from memory 153, and may form a plurality of packets. In some embodiments, for each master segment obtained one packet is formed. In some embodiments, each packet may be used to define a pulse segment. Pulse segments may be concatenated to form a desired waveform. Each pulse segment of the waveform may be locked to a voltage defined by the reference voltage contained in the respective packet.

In some embodiments, the packet may be transmitted through delay mesh circuit 269. In some embodiments, delay mesh circuit 269 may receive one or more packets from the packet generators, and may generate a plurality of copies of the packets. For example, delay mesh circuit 269 may generate, for each pulser, one copy of the packet. In some embodiments, delay mesh circuit 269 may transmit the copies with one or more time delays. For example, the copies may be time delayed based on a desired distribution.

At act 408, the decoding circuitry, comprising decoding circuits $105_1 \ldots 105_N$ may receive the serialized packets and decode them. Decoding the serialized packet may comprise performing a serial-to-parallel conversion in some embodiments. Accordingly, the decoding circuits may receive the packet one bit at a time, and may form one or more words of bits. For example, one word may comprise a field, such as field $312_B$, containing bits defining a reference voltage. In some embodiments, the word corresponding to the reference voltage may be transmitted in parallel by the encoding circuits to respective pulsing circuits.

In some embodiments, decoding the serialized packet may comprise modulating the packet. The packet may be modulated by multiplying, or dividing, the value of the packet corresponding to the reference voltage by a desired factor. In some embodiments, the various packets received by the decoding circuits may be modulated with different factors. For example, the packets may be modulated according to a desired modulation profile, such that each decoding circuit may provide a desired factor. In some embodiments, modulation of the packets may be performed to obtain a spatially apodized pulse across the array of ultrasonic transducers.

At act 410, pulsing circuits $103_1 \ldots 103_N$ may be controlled by respective decoding circuits $105_1 \ldots 105_N$. As described above, control of the pulsing circuits may be obtain by providing fields $312_A$, $312_B$ and $312_C$ to the pulsing circuits. In response to obtaining the fields, the pulsing circuits may generate a pulse segment. The fields may be received through words transmitted in parallel in some embodiments. In some embodiments, the pulse segment may have a voltage that is locked to the reference voltage received. The reference voltage may, or may not, be scaled by a modulation factor.

At act 412, the pulse segment may be transmitted to an ultrasonic transducer. In response, the ultrasonic transducer may generate an acoustic ultrasound waveform segment. In some embodiments, the acoustic ultrasound waveform segment may have an intensity that is proportional to the locked voltage. In some embodiments, packets may be concatenated to form a waveform having a plurality of pulse segment. Correspondingly, an acoustic ultrasound waveform having a plurality of acoustic ultrasound waveform segments may be formed.

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Aspects of the present application provide pulsing circuits configured to generate multi-level pulses that may that may improve the quality of ultrasound images by providing spatial and/or temporal apodization. Apodization may reduce the extent of the side-lobes associated with transmitted pulses, thus increasing the resolution of the image produced.

Aspects of the present application provide software-defined waveform generators. Waveform generators of the type described herein may be configured to control the pulsing circuits in response to the execution of a computer code. The use of waveform generators of the type described herein may significantly lessen the hardware required to generate ultrasound pulses, and thus may decrease the power consumption and/or the real estate required.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, and/or methods described herein, if such features, systems, articles, materials, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

The invention claimed is:

1. A method of controlling a pulser coupled to an ultrasonic transducer, the method comprising:
    selecting, with a packet generator, a subset of master segments from a plurality of master segments stored in a memory on a handheld ultrasound probe, the plurality of master segments indicating a plurality of selectable reference voltages, and the subset of master segments including a first master segment indicating a first reference voltage and a second master segment indicating a second reference voltage;
    generating, with the packet generator, a succession of packets based on the subset of master segments, wherein generating the succession of packets defines an order for the succession of packets and comprises:
        generating, from the first master segment, a first data packet in the succession of packets with the packet generator, the first data packet comprising a first value representing the first reference voltage and a second value representing a first duration of a first pulse segment; and
        generating, from the second master segment, a second data packet in the succession of packets with the packet generator, the second data packet comprising a third value representing the second reference voltage and a fourth value representing a second duration of a second pulse segment;
    subsequent to generating the first data packet with the packet generator, encoding the first data packet with encoding circuitry on the handheld ultrasound probe;
    subsequent to encoding the first data packet, generating, with delay circuitry on the handheld ultrasound probe, a plurality of time-delayed versions of the first data packet;
    providing the plurality of time-delayed versions of the first data packet to decoding circuitry on the handheld ultrasound probe;
    subsequent to providing the plurality of time-delayed versions of the first data packet to the decoding circuitry, decoding the plurality of time-delayed versions of the first data packet with the decoding circuitry on the handheld ultrasound probe;
    subsequent to decoding the plurality of time-delayed versions of the first data packet with the decoding circuitry, transmitting one of the plurality of time-delayed versions of the first data packet to the pulser, the pulser being coupled to the ultrasonic transducer on the handheld ultrasound probe;
    in response to the transmitting of the one of the plurality of time-delayed versions of the first data packet to the pulser, setting the pulser to a first state corresponding to the first reference voltage throughout the first duration of the first pulse segment;
    subsequent to generating the second data packet with the packet generator, encoding the second data packet with the encoding circuitry on the handheld ultrasound probe;
    subsequent to encoding the second data packet, generating, with the delay circuitry on the handheld ultrasound probe, a plurality of time-delayed versions of the second data packet;
    providing the plurality of time-delayed versions of the second data packet to the decoding circuitry on the handheld ultrasound probe;
    subsequent to providing the plurality of time-delayed versions of the second data packet to the decoding circuitry, decoding the second data packet with the decoding circuitry on the handheld ultrasound probe;
    subsequent to decoding the plurality of time-delayed versions of the second data packet with the decoding circuitry, transmitting one of the plurality of time-delayed versions of the second data packet to the pulser on the handheld ultrasound probe;
    in response to the transmitting of the one of the plurality of time-delayed versions of the second data packet to the pulser, setting the pulser to a second state corresponding to the second reference voltage throughout the second duration of the second pulse segment;
    wherein the plurality of selectable reference voltages comprises at least three reference voltages; and
    wherein the one of the plurality of time-delayed versions of the first data packet and the one of the plurality of time-delayed versions of the second data packet are transmitted serially.

2. The method of claim 1, further comprising generating an acoustic ultrasound waveform segment using the ultrasonic transducer, in response to setting the pulser to the first state, wherein the acoustic ultrasound waveform segment has a magnitude that is determined by the first reference voltage.

3. The method of claim 1, wherein the pulser comprises a first transistor and a second transistor, and wherein the first data packet comprises a value representing a first conductive state associated with the first transistor and a second conductive state associated with the second transistor; and wherein setting the pulser to the first state comprises causing the first transistor to assume the first conductive state and the second transistor to assume the second conductive state based on the value representing the first conductive state associated with the first transistor and the second conductive state associated with the second transistor.

4. The method of claim 1, further comprising modulating the first data packet to obtain spatial apodization.

5. The method of claim 1, further comprising providing a bipolar waveform to the ultrasonic transducer using the pulser.

* * * * *